(12) United States Patent
De Haas et al.

(10) Patent No.: US 10,960,183 B2
(45) Date of Patent: Mar. 30, 2021

(54) DEFLECTABLE DEVICE WITH ELONGATE ACTUATOR

(71) Applicant: KONINKLIJKE PHILIPS N.V., Eindhoven (NL)

(72) Inventors: Cornelis Gerardus Maria De Haas, Nuenen (NL); Johannus Gerardus Van Beek, Budel (NL); Rudolf Maria Jozef Voncken, Eindhoven (NL); Jacob Roger Haartsen, Eindhoven (NL); Franciscus Reinier Antonius Van Der Linde, Schijndel (NL); Franciscus Johannes Gerardus Hakkens, Eersel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 103 days.

(21) Appl. No.: 16/308,510

(22) PCT Filed: Jun. 28, 2017

(86) PCT No.: PCT/EP2017/066059
§ 371 (c)(1),
(2) Date: Dec. 10, 2018

(87) PCT Pub. No.: WO2018/002179
PCT Pub. Date: Jan. 4, 2018

(65) Prior Publication Data
US 2019/0151617 A1    May 23, 2019

(30) Foreign Application Priority Data

Jun. 29, 2016 (EP) ..................... 16176987

(51) Int. Cl.
*A61M 25/01* (2006.01)
*A61B 1/00* (2006.01)
*A61M 25/09* (2006.01)

(52) U.S. Cl.
CPC ..... *A61M 25/0158* (2013.01); *A61B 1/00147* (2013.01); *A61M 2025/09141* (2013.01); *A61M 2205/0266* (2013.01)

(58) Field of Classification Search
CPC .... A61M 25/0158; A61M 2025/09141; A61M 2205/0266; A61B 1/00147
See application file for complete search history.

(56) References Cited

U.S. PATENT DOCUMENTS

| 4,799,474 A * | 1/1989 | Ueda ................... A61B 1/0058 |
| | | 600/133 |
| 4,930,494 A | 6/1990 | Takehana |
| 8,647,297 B2 | 2/2014 | Kronstedt |
| (Continued) | | |

FOREIGN PATENT DOCUMENTS

WO    2015055413 A1    4/2015

*Primary Examiner* — Amber R Stiles (57) ABSTRACT

A deflectable device (100) comprising an elongate body (110) and a folded elongate member (120) is configured to change an orientation of the distal portion (114) of the elongate body (110) with respect to the proximal portion (112) of the elongate body (110) upon an electrical current flowing through the folded elongate member (120) causing a change of a length of the folded elongate member (120).

11 Claims, 4 Drawing Sheets

(56) References Cited

U.S. PATENT DOCUMENTS

| | | | |
|---|---|---|---|
| 2004/0087939 A1* | 5/2004 | Eggers | A61B 18/1206 606/41 |
| 2006/0064055 A1* | 3/2006 | Pile-Spellman | A61M 25/0105 604/95.05 |
| 2012/0123326 A1 | 5/2012 | Christian | |
| 2015/0265345 A1 | 9/2015 | Bui | |

* cited by examiner

DEFLECTABLE DEVICE WITH ELONGATE ACTUATOR

CROSS-REFERENCE TO PRIOR APPLICATIONS

This application is the U.S. National Phase application under 35 U.S.C. § 371 of International Application No. PCT/EP2017/066059, filed on Jun. 28, 2017, which claims the benefit of European Patent Application No. 16176987.2, filed on Jun. 29, 2016. These applications are hereby incorporated by reference herein.

FIELD OF THE INVENTION

The present invention relates to the field of deflectable devices. More specifically it relates to deflectable devices steered by application of an electrical current.

BACKGROUND OF THE INVENTION

Minimally Invasive Vascular Surgery (MIVS) is widely adopted and often preferred above open surgery for its smaller incisions, less blood loss, reduced risk of infection, decreased pain and quicker recovery. Within this field, various surgeries are performed using minimally invasive instruments such as catheters, sheaths, and guidewires, under fluoroscopic guidance.

Device maneuverability has a strong influence on both the procedure time (and therefore also X-ray doses and cost) as well as the risk of complications such as perforation. However, conventional devices are often difficult to maneuver and control, for the following reasons:

The contact friction between the device and vessels may cause stick-slip phenomena, leading to hysteresis and sudden jumps in tip movement, with reduced control of the tip as a consequence. Hence, some locations are unreachable or are only reached after a lengthy procedure.

Conventional devices have a fixed stiffness and fixed distal shape. Therefore, in order to reach the desired location, surgeons often have to use trial-and-error to choose the device with the correct stiffness and distal shape. Again, such device replacements lead to extended operating times, with accompanying increase of X-ray and contrast agent doses. In addition, the repeated extraction and insertion can do serious harm to the patient and increase the risk of infection.

Steerable catheters may overcome the above limitations by the ability to vary their distal shape and distal bending stiffness to improve maneuverability by their flexibility in shape to adapt to patient anatomy. Currently available manually operated steerable catheters are all based on pull-wire steering. Typical examples are steerable radiofrequency (RF) ablation catheters, mapping catheters used in electrophysiology.

A pull-wire based steerable catheter has one or more pull-wires running along the length of the catheter. At the distal end, the pull-wires are fixed to the catheter tip offset from the neutral line to be able to apply a bending moment, whereas at the proximal end they are mounted to an actuation mechanism in the catheter handle for manual control of the pulling force. Since the catheter tip is designed such that it is much more flexible than the shaft, the tip bends whereas the shaft remains nearly unbent upon pulling one of the pull-wires.

To increase the flexibility and maneuverability of the catheters, shape memory alloy (SMA) actuators are being developed. Steerable catheters based on shape memory alloy steering have potentially lower shaft stiffness.

US 2006/0064055 discloses a steerable device comprising a plurality of SMA wires having a graded, essentially non-constant cross sectional area that increases between the distal and proximal ends of the steerable device. The SMA wire having a first cross sectional area at least of smaller diameter or cross sectional area, will heat up faster, due to higher resistance. As current increases, the end with smaller cross sectional area will reach the transformation temperature first and change to its predetermined shape before the end of the larger diameter.

U.S. Pat. No. 4,930,494 discloses an insertion section of an endoscope comprising pair of SMA coils arranged symmetrically along and with respect to the axis of the segment of the insertion section of the endoscope. The SMA coils are supplied with current from a supply unit through lead wires. As result, the heated SMA coils are displaced so as to be restored to the memorized close-winding state. The insertion section of an endoscope is bent toward the energized coil form the pair of coils.

However, integration of shape memory alloy actuators in catheters (or guidewires) is complex.

SUMMARY OF THE INVENTION

It is an object of the present invention to provide a deflectable device with a less complex construction.

According to the invention, this object is realized by a device comprising:

a flexible elongate body;

at least an electrically conductive folded elongate member eccentrically positioned within the flexible elongate body to a longitudinal axis of the flexible elongate body;

wherein a first portion of the folded elongate member is fixedly secured to a proximal portion of the flexible elongate body and a second portion of folded elongate member is fixedly secured to a distal portion of the flexible elongate body; and wherein the device is configured to change an orientation of the distal portion of the elongate body with respect to the proximal portion of the elongate body upon an electrical current flowing through the folded elongate member causing a change of a length of the folded elongate member.

The advantage of the electrically conductive folded elongate member integrated in the device is that electrical connection to the actuating part providing the deflection of the device is realized at the proximal portion of the device, at the ends of the legs of the folded elongate member. This significantly simplifies the construction of the device, due to the fact that the technical specifications of the distal portion of deflectable devices are application specific, and for instance comprise a diameter constraint, which is difficult to achieve with conventional constructions requiring electrical connections in the distal portion of the deflectable device. The folded elongate member can be regarded as an elongate actuator, hence the first portion of the folded elongate member is the proximal side of the elongate actuator, whereas the second portion is the distal side of the elongate actuator, resulting that the elongate actuator is fixedly secured to the flexible elongate body at two distinct portions, one located distal to the other.

As no electrical connection to the power supply needs to be provided at the distal portion of the device according to the invention, this makes integration of the folded elongate member as actuating part of the device much easier, resulting in a lower integration cost, and in a more reliable performance of the deflectable device.

The effect of a change of the length of the folded elongate member can be realized in two different ways. An electrically conductive material through which an electrical current passes can expand or shrink due to resistive heating. A first category of materials that can be used for the folded elongate member is formed by metals (e.g. Al, Cu, etc.) and metal alloys (e.g. steel, etc.) presenting expansion upon resistive heating. A metallic folded elongate member eccentrically positioned to the longitudinal axis of the device pushes the distal portion of the device from the neutral position along the longitudinal axis of the device in the direction opposite to the position of the folded elongate member with respect to the longitudinal axis of the device.

In an embodiment of the device the folded elongate member is a shape memory alloy material (SMA). The most commonly used SMA materials shrinking upon resistive heating are the Cu—Al—Ni and Ni—Ti alloys. An SMA folded elongate member eccentrically positioned to the longitudinal axis of the device pulls the distal portion of the device from the neutral position along the longitudinal axis of the device toward the position of the folded elongate member. An electrical connection (e.g. through a Cu wire) to the distal end of a straight SMA elongate member would result in an undefined thermal contact with the shape memory alloy material leading to instable performance. The SMA elongate member running along the metallic wire connecting the distal portion of the SMA elongate member would reduce the degree of deflection of the device due to the fact that a resistive heating of the metallic wire causes expansion of the metallic wire, while the SMA elongate member shrinks upon resistive heating. Furthermore, SMA materials are particularly difficult to solder and to realize reliable electrical connection with metallic conductors. As no electrical connection needs to be provided at the distal portion of the embodiments according to the invention, the area taken by the folded elongate member responsible for the deflection of the device can be reduced, influencing the total diameter of the flexible elongate body (e.g. catheter) less. Therefore, it is an advantage of embodiments of the present invention that they have an increased performance with a better controlled, smoother/more continuous actuation.

In an embodiment of the device at least a leg of the folded elongate member is embedded in electrically insulating material. This allows the use of other electrically conductive parts in the construction of the device for providing additional functionalities to the device (e.g. electrical signal measurements or providing electrical current locally to an object or tissue), without crosstalk between operation of the folded elongate member responsible for the actuation of the device and the operation of the additional diagnostic or treatment functionalities. Furthermore, the electrical insulating material ensures that the electrical current is flowing through the folded elongate member form the electrical connection at the first leg of the folded elongate member to the electrical connection at the second leg, thereby maximizing the actuation potential of the folded elongated member.

In an embodiment the device comprises multiple folded elongate members. A smaller diameter of the flexible elongate body is especially advantageous for microcatheters, for instance in case of bending in multiple directions that requires more actuators. It is an advantage of the embodiment of the present invention that the electrical connections with the elongate actuator can be made at the proximal end so that the electrical connection wire is not disturbing the performance of the folded elongate members, wherein mechanical and thermal disturbing effects are considered. It is further an advantage of the embodiment of the present invention that the tip of the device (the non-bendable, distal part) is shorter due to the improved mechanical fixation. It is an advantage of the embodiment of the present invention that the elongate parts can be positioned such that bending of multiple segments is possible. This can for example be advantageous when patient anatomy demands more complex device shapes for proper navigation. It is an advantage of the embodiment of the present invention that the good control of the elongate actuators, the multiple folded elongate members, on the bending of the flexible elongate body allows to use an elongate body with a smaller stiffness than when using a pull-wire based catheter. The reason therefore being that in pull-wire based catheters the pulling force which is applied at the proximal end needs to be transmitted by the pull-wire assembly to the distal end of the catheter. Therefore, the bending stiffness of the shaft needs to be relatively high to enable bending of the tip segment while the shaft remains unbent.

In an embodiment the device comprises an electrical connection of the distal ends of the multiple folded elongate members. It is an advantage of the embodiment of the present invention that multiple paths are created for the electrical current flowing through the interconnected distal portions of the multiple folded elongate members, and therefore the device can be deflected in multiple directions.

In an embodiment of the present invention the folded elongate member is a flat wire or a strip. A strip or flat wire may increase the strength (and hence the force that can be generated) with a smaller increase of the total diameter of the device than in case a wire would be used. This can for example be useful in an application where quite high forces are needed. In that case strong elongate parts are required. This could be achieved by making a wire thicker, which leads to a larger diameter of the device. An alternative would be to use a flat wire or strip. In some cases it could be a benefit that the force increases but that the device stays flexible in one direction by applying a flat wire or a strip.

In another aspect of the invention a system is presented, comprising:

a power control unit for providing electrical current;

the device according to the invention, wherein two legs of the at least one folded elongate member are adapted to be electrically connectable to the power control unit. In a further embodiment:

the device comprises multiple folded elongate members electrically connected at a distal portion;

each leg of the multiple folded elongate members is adapted to be electrically connectable to the power control unit;

the power control unit is configured to provide electrical current selectively to the legs of the multiple elongate members.

It is an advantage of the embodiment of the present invention that the direction and/or the magnitude of the resulting force on the elongate body orthogonal to the longitudinal axis of the elongate body can be controlled by controlling the current through the different legs of the elongate actuators (multiple folded elongate members). It is an advantage of the embodiments of the present invention that different currents can be transmitted through the legs. For instance in the case when the multiple folded elongate members are of SMA material, a current through a first leg in a first direction can for example return through two other legs in the opposite direction. The current in the first leg is higher and thus may cause shortening of the first leg, which may be larger than the shortening of the other legs. The heating of the other legs caused by the current flowing through them may even not be high enough to cause shortening (shrinking) of these other legs. This is the case when the temperature stays below the SMA transformation temperature.

In a different aspect of the invention a method is presented, comprising:

providing a deflectable device according to the invention;

controlling the electrical current provided to the at least a folded elongate member within the device to change the orientation of the distal portion of the elongate body with respect to the proximal portion of the elongate body upon an electrical current flowing through the folded elongate member causing a change of a length of the folded elongate member. It is an advantage of the method that the deflection of the device is better controlled, is smoother and more continuous.

Additional aspects and advantages of the invention will become more apparent from the following detailed description, which may be best understood with reference to and in conjunction with the accompanying drawings.

Any reference signs in the claims shall not be construed as limiting the scope.

In the different drawings, the same reference signs refer to the same or analogous elements.

DETAILED DESCRIPTION OF EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Figure 1:
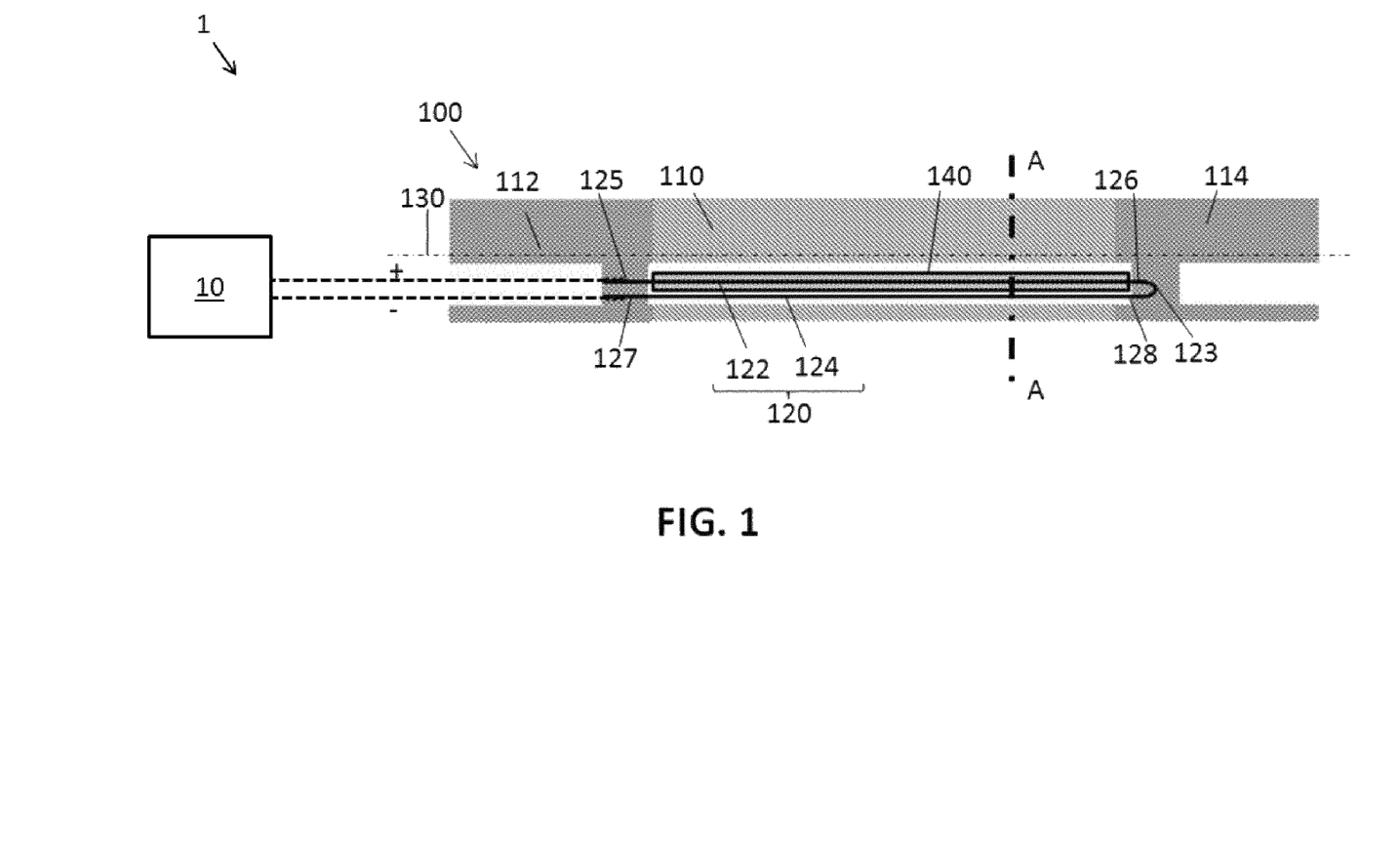
FIG. 1 shows schematically a system for deflection of a device, wherein a longitudinal cross section of the device according to the invention is illustrated.

An example of a system 1 for deflection of a device 100 is illustrated in FIG. 1. The deflectable device 100 has a flexible elongate body 110 comprising a proximal portion 112 and a distal portion 114. Alternatively, the flexible elongate body 110 comprises a more flexible segment between the proximal portion 112 and the distal portion 114 of stiffer segments. FIG. 1 also shows an elongate actuator 120, in a form of a folded elongate member, comprising a first elongate part 122 and a second elongate part 124, with two electrical contacts at a first side 125, 127 and with, in the example illustrated, a fold 123 at the opposite second side 126, 128 of the elongate actuator 120. The first elongate part 122 is embedded in an insulator 140. The elongate actuator 120 is positioned off-axis with regard to the longitudinal axis 130 of the deflectable medical device 100. Therefore, in operation, the deflectable device 100 (e.g. catheter) bends as result of shrinkage or expansion of one or more elongate parts 122, 124 of the elongate actuator 120. In the exemplary embodiment, the elongate parts 122, 124 of the elongate actuator 120 are positioned in one lumen 200, i.e. hollow space, of a catheter. Such a catheter may have additional lumens not comprising an elongate actuator. The first and second elongate parts 122,124 of one actuator 120, the two legs of the folded elongate member, are positioned within one lumen. Alternatively, they may be positioned in different lumens. By carefully positioning the elongate parts of the elongate actuators, different bending directions and different bending sections of the flexible elongate body 110 (e.g. catheter) can be achieved. In the exemplary embodiment the elongate actuator 120 is fixed in a re-molten (reflow) polymer of the flexible elongate body 110 at its proximal and distal ends. The folded elongate member 120 is electrically connected to a power control unit 10 at its proximal end, specifically at the proximal ends of the legs 122,124 of the folded elongate member 120.

Figure 2:
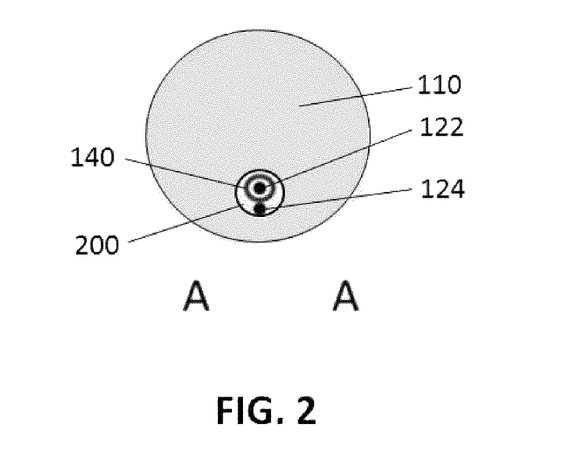
FIG. 2 schematically shows a transversal cross section of the same deflectable device as in FIG. 1.

FIG. 2 shows schematically the cross section of the same deflectable device as the device 100 illustrated in FIG. 1. The cross section is taken at position AA illustrated in FIG. 1. The cross section shows the flexible elongate body 110, the first elongate part 122 and the second elongate part 124 of the elongate actuator 120, positioned off axis in the elongate body 110. The first elongate part 122 is embedded in an insulator 140. Both, the first elongate part 122 and the second elongate part 124 are provided in a lumen 200 in the flexible elongate body 110.

In embodiments of the present invention the elongate actuator 120 is a U-shaped SMA element positioned off-axis in a deflectable device 100 implemented as a catheter, such that the two free ends (the first sides 125,127) of the SMA element are electrically connectable at the proximal portion of the deflectable medical device 100 (e.g. catheter) to a conductive connection wire 325, 327, e.g. a metallic connection wire such as for instance a Cu wire. In embodiments of the present invention, the elongate actuator 120 is fixed with the first sides 125, 127 to the proximal portion 112 of the flexible elongate body 110. The opposite sides 126, 128 with the fold 123 of the elongate actuator 120 are fixed to the distal portion 114 of the flexible elongate body 110. Since no conductive, e.g. metallic, connection wire runs along the elongate body 110, exposure of such a conductive, e.g. metallic, wire to repetitive tensile and compressive stresses is avoided.

Figure 3:
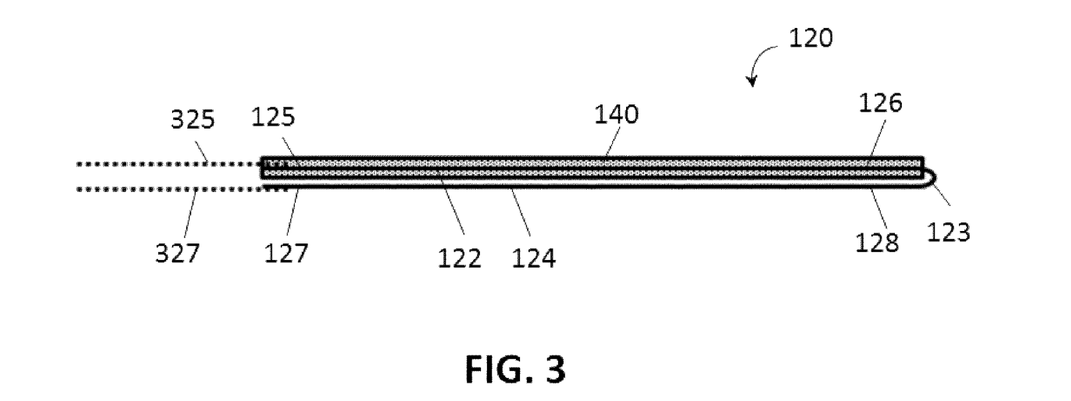
FIG. 3 schematically shows a folded elongate member with one leg insulated, in accordance with embodiments of the present invention.

FIG. 3 schematically illustrates an elongate actuator 120 in accordance with embodiments of the present invention. The elongate actuator 120 comprises a first elongate part 122 and a second elongate part 124. Both elongate parts have a first side 125, 127 and an opposite second side 126, 128. The elongate actuator 120 is folded over a bend or fold 123. The elongate actuator 120 can be integrated in the flexible elongate body 110 with the fold closest to the distal end of the elongate body 110. The fold (bend) 123 at the distal end will be much better fixed after reflow of the catheter polymer or after fixation by gluing, compared to a single SMA wire which is connected with a copper wire as in the prior art implementation illustrated in FIG. 5. Therefore, the risk of failure during operation is smaller for medical devices according to embodiments of the present invention. In embodiments of the present invention the deflectable device may be an intravascular catheter. Such a catheter may be made of a polyether block amide (a block copolymer). By changing the composition, different grades with different hardness can be made. The elongate actuator may for example comprise a long unactuated shaft which is made of stiff material and an actuated tip which is made of more flexible material. In embodiments of the present invention the lumens may have a thin PTFE layer on the outside diameter (OD) of the lumen. The layer is called a PTFE liner.

In this example illustrated in FIG. 3, the first elongate part 122 is insulated, by embedding or covering the first elongate part 122 by an insulator 140. The first and second elongate parts 122, 124 are made of a shape memory alloy. In this example electrical wires 325,327 are electrically connected to the first sides 125, 127.

The elongate parts 122, 124 can be made in different shapes. They can for example be wire shaped, coil shaped, they can be flat wires or they can be elongate strips. Depending on the application one shape may be more appropriate than the other. A wire has a small diameter, a coil can generate more strain but less force. As explained before, flat wires and strips can be applied if a higher force is needed without adding too much to the diameter of the catheter.

A power supply (not illustrated) can be connected to the first sides 125, 127, e.g. by means of the electrical wires 325, 327. In operation, once electrical power is applied, e.g. a voltage is applied, an electrical current will flow through the elongate actuator 120 and it will cause resistive heating of the legs 122,124 of the folded elongate member 120. As a result thereof, the length of the shape memory alloy, of which the elongate actuator 120 is made, will change. The shape memory alloy may for example change from the detwinned martensite phase to the austenite phase resulting in a shrink of the SMA between 3 and 7%. In embodiments of the present invention the shape memory alloy may for example be nitinol (nickel titanium alloy). Alloys with small adaptations in the composition may be used to improve for instance the control of the elongate actuator (e.g. by having an SMA material with less hysteresis). Because the elongate actuator 120 is attached at particular locations to the flexible elongate body 110, a shrinking of the elongate actuator 120, placed off-axis in the elongate body 110, will cause a deformation in this flexible body 110, and thus a bending thereof, or at least of the distal portion 114 thereof.

Figure 4:
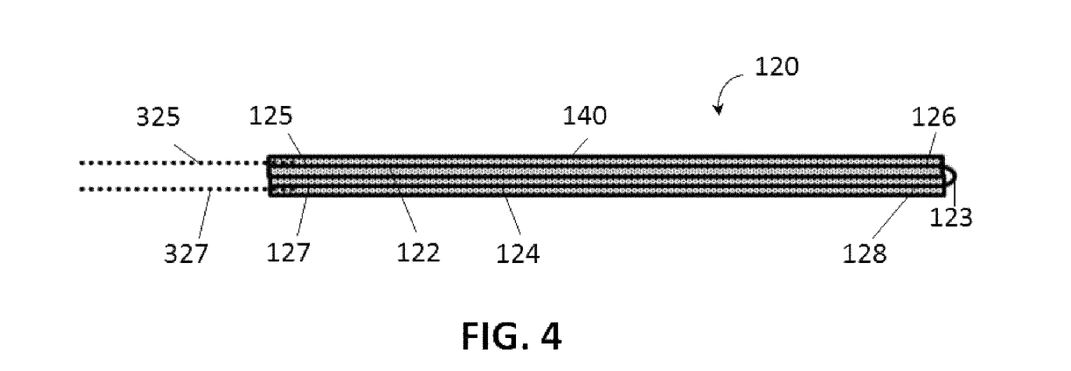
FIG. 4 schematically shows a folded elongate member having two insulated legs, in accordance with embodiments of the present invention.

FIG. 4 shows a similar elongate actuator 120 as FIG. 3. In this elongate actuator 120, not only the first elongate part 122 but also the second elongate part 124 is insulated. Different types of insulating material such as a PTFE (polytetrafluoroethylene) liner can be used for insulating the first and/or second elongate part 122, 124 of the elongate actuator 120. Insulating both elongate parts requires a larger lumen, which can sometimes be critical like for microcatheters which have to be very thin. Insulating both elongate parts can be beneficial as both wire sections have the same thermal insulation around them, and therefore a more equal temperature, which makes them easier to control. In embodiments of the present invention the first and second elongate parts are insulated (e.g. with a PTFE tube) before obtaining the elongate actuator 120 by folding. After folding, the insulation, e.g. the PTFE, at the bend 123 is preferably removed to improve the fixing of the elongate actuator in the distal portion 114 of the elongate body 110.

Figure 5:
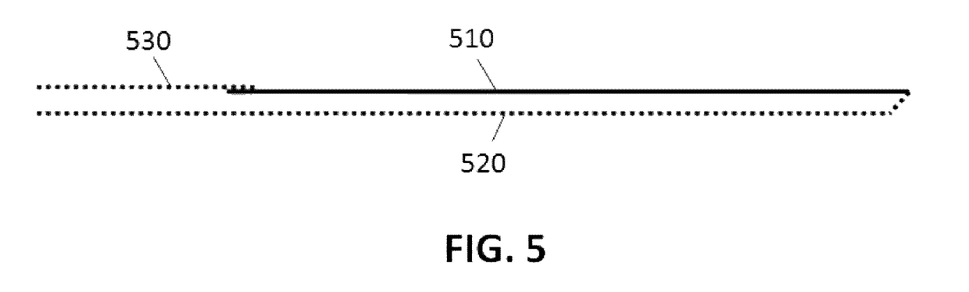
FIG. 5 schematically shows a prior art SMA actuator.

FIG. 5 schematically illustrates a prior art SMA wire actuator, for comparison and instruction purposes only. This actuator 510 has electrically conductive wires 520, 530 connected at both its distal and its proximal end. During actuation, the SMA wire 510 shrinks. However, the electrical connect wire does not shrink and hinders SMA wire shrinkage. This effect is even stronger in a small diameter lumen than in a catheter or guided wire.

In contrast, embodiments of the present invention (FIG. 3 and FIG. 4) have an elongate actuator 120 comprising a first elongate part 122 and a second elongate part 124 wherein both parts are made of SMA and hence wherein both parts are shrinking when a current is flowing through them. Therefore, the actuation is better controlled and smoother/more continuous than in an actuator as illustrated in FIG. 5. Furthermore, in embodiments implementing a bent elongate actuator, as illustrated in FIG. 3 and FIG. 4, the connection (i.e. the bend) between the first and the second elongate part 122, 124 may be stronger than the connection made between SMA wires as the first and second elongate parts, and a conductive wire, e.g. a metallic wire such as a copper wire at the distal end.

Figure 6:
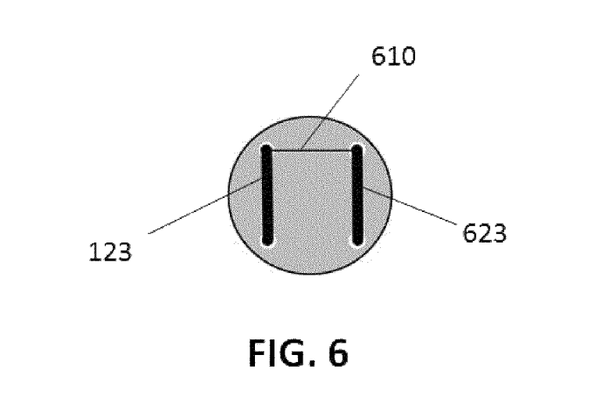
FIG. 6 schematically shows the folds of two elongate actuators of a device comprising two elongate actuators, in accordance with embodiments of the present invention.

FIG. 6 schematically illustrates the folds 123, 623 of two elongate actuators of a medical device in accordance with embodiments of the present invention. The figure shows a first bend 123 of a first elongate actuator 120, and a second bend 623 of a second elongate actuator at the distal end of the deflectable medical device. The bends of both elongate actuators are electrically interconnected using an electrical connection 610. The electrical connection 610 can for example interconnect the second end of an elongate part of the first elongate actuator 120 and the second end of an elongate part of the second elongate actuator. The electrical connection 610 can be realized by applying the electrical connection (e.g. soldering wires at the folds 123 and 623) before the folded elongate members 120,620 are introduced into the flexible elongate body, after which fixing the proximal sides and the distal sides of the folded elongate members is achieved by re-flow of the flexible elongate body material at the desired portions. Alternatively, an electrically conductive plate (or wire) at the distal end of the lumen 200 hosting the folded elongate members may be used for electrical connection of the folds 123 and 623 of the folded elongate members 120,620. In this case the folded elongate members 120,620 are introduced into the lumen 200 of the elongate body 110 to the distal end of the lumen 200, where the folds 123,623 reach the electrically conductive plate, and then subsequently the proximal sides and the distal sides of the folded elongate members are securely fixed by re-flow of the flexible elongate body material at the desired portions.

In another aspect, embodiments of the present invention relate to a method for deflecting a medical device, more particularly a deflectable device 100 according to embodiments of the first aspect of the present invention. For this method the device comprises multiple electrically conductive folded elongate members. The current through the elongate parts of the elongate actuator is controlled such that the current through at least one leg of the folded elongate members is higher than the current through the other legs.

Figure 7:
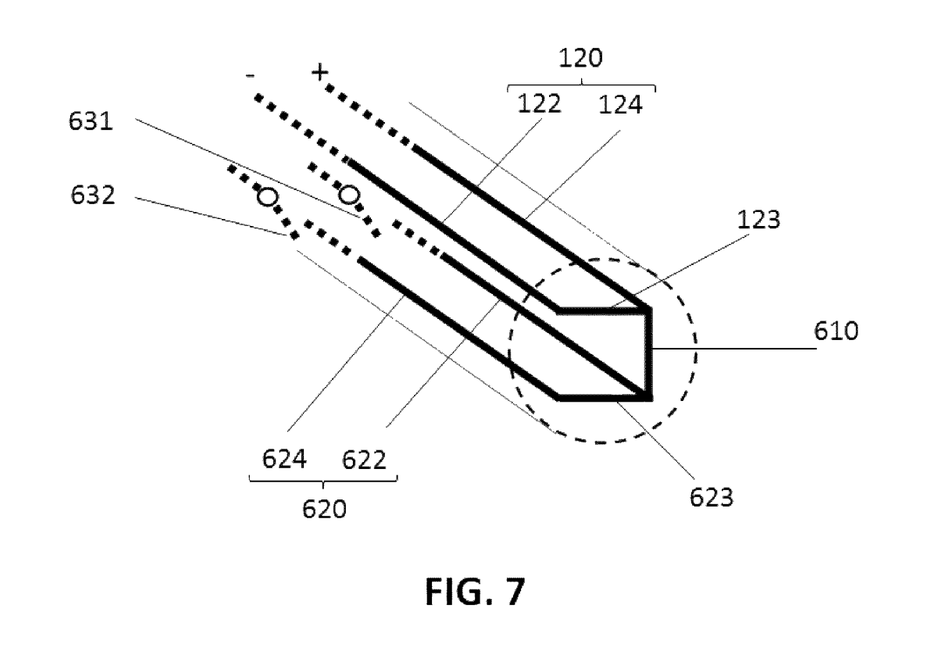
FIG. 7 schematically shows a 3D-view of a device comprising two actuators with two electrically connected first sides and with two floating first sides in accordance with embodiments of the present invention.
Figure 8:
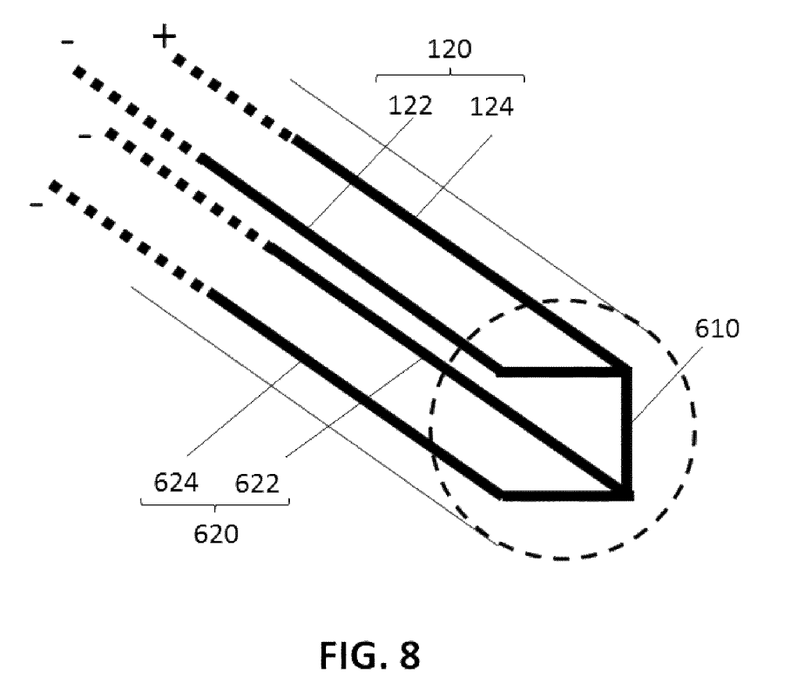
FIG. 8 schematically shows a 3D-view of the same device as in FIG. 7, but with three first sides connected to the negative pole of a power supply and with one first side connected to the positive pole of a power supply, in accordance with embodiments of the present invention.

An example of such a method is elucidated herein below. This method is applied to a deflectable medical device as illustrated in FIG. 6, FIG. 7 and FIG. 8. These devices include an elongate actuator formed by a plurality of folded elongate members that are electrically interconnected at the distal portion. In embodiments of the present invention, illustrated in the drawings, two folded elongate actuators are electrically connected to one another at the level of their folds. The folds 123 of the folded elongate actuators are interconnected using an electrical connection 610. This enables multiple steering directions without having electrical connect wires running from the distal portion of the device to its proximal portion. At the proximal part, different voltages can be applied between the legs of the folded elongate members, or some of the legs of one or more folded elongate members can be left floating.

Examples of such a structure are shown in FIG. 7 and in FIG. 8. FIG. 7 shows a schematic 3D-view of a medical device comprising two elongate actuators 120, 620, each having two elongate parts 122, 124 and 622, 624, respectively. The elongate parts 122, 124, 622, 624 are all electrically connected to one another at their second side (distal end), and are all electrically separate at their first side (proximal end). In the example illustrated, two of the elongate parts 122, 124 forming one of the elongate actuators 120 are electrically connected to a power control unit 10 (electrical power supply) at their first sides and the other two elongate parts 622, 624 are left floating at their first sides. The figure shows a first elongate actuator 120 comprising a first elongate part 122 and a second elongate part 124, a second elongate actuator 620 comprising a first elongate part 622 and a second elongate part 624, and shows two open electrical switches 631, 632. The second elongate part 124 of the first elongate actuator is electrically connected with the second elongate part 624 of the second elongate actuator by an electrical connection 610. The elongate parts are positioned such that, when selectively running a current through some of these parts, shrinking of these parts causes a resulting force on the elongate body orthogonal to the longitudinal axis. In this example, the elongate parts 122, 124, 622, 624 are all at the same distance from the longitudinal axis of the deflectable medical device. In this example the angle between neighboring planes formed by the elongate parts and the longitudinal axis is 45°. The invention is, however, not limited thereto and any other suitable configuration for bending the medical device at a certain place in a certain direction is possible. In this example, the electrical switches 631, 632 are open and a power supply is connected with the positive pole to the first side of the second elongate part 124, and with the negative pole to the first side of the first elongate part 122 of the first elongate actuator 120. This results in a current through the first elongate actuator which causes shrinking of this actuator, which causes bending of the elongate medical device. The connection with the first sides of the elongate parts may be made in a handle of the deflectable medical device or by electronics of the deflectable medical device.

FIG. 8 shows a schematic 3D-view of the same medical device as in FIG. 7, but with three first sides of the three elongate parts 122, 622, 624 connected to the negative pole of a power supply and with one first side of one elongate part 124 connected to the positive pole of a power supply, in accordance with embodiments of the present invention. In this example, current flows in one direction through a first elongate part of an elongate actuator and flows through the three remaining elongate parts in the other direction. Thereby the current through the first elongate part is high enough to cause heating of the elongate part above the transformation temperature of the SMA (the austenite transformation temperature). The current through the three remaining elongate parts in the other direction is heating these elongate parts but not to the same extent, in particular not above the transformation temperature of the SMA. Thus only the first elongate part 124 is shortening due to the applied voltage. This shortening causes a resulting force to the elongate body orthogonal to the longitudinal axis of the deflectable medical device.

When using full actuation or no actuation of the elongate parts of the actuators in the examples illustrated in FIG. 7 and FIG. 8, such a structure allows deflection of the flexible elongate body 110 in eight different directions. Firstly, two neighboring elongate parts can be activated by connecting them to different voltages. In this way the flexible elongate body 110 can be deflected in 4 directions. Secondly, by actuating a single elongate part the elongate body can be deflected in 4 other directions. These directions differ 45 degrees from the first mentioned directions.

In order to prevent stresses hampering deflection of the distal portion of the elongate body with respect to the proximal portion of the elongate body it is an option to, for instance, fully actuate the first elongate part 122 of the first elongate actuator 120, half actuate the second elongate part 124 of the first elongate actuator 120 and the second elongate part 624 of the second actuator 620, and not actuate the first elongate part 622 of the second elongate actuator 620.

It is an advantage of embodiments of the present invention that many more directions can be realized by using different partial actuation levels of the folded elongate members by applying the appropriate voltage differences to the legs of the multiple folded elongate members, resulting in different current (and heating levels) of the legs enabling a continuous (step free) movement in all directions.

The elongate actuators may for example be applied in steerable catheters, guided wires, (introducer) sheaths.

Medical devices according to embodiments of the present invention may comprise a computer readable medium having stored a computer-executable program for deflecting a medical device. The computer program comprising program code means for causing the deflectable device to carry out a method controlling the current through the elongate parts of the elongate actuator, when the computer program is run on a computer of a control unit controlling the deflectable device. The method may be adapted to send a higher current though one elongate part and a lower current through another elongate part as explained above.

Although a deflectable medical device is used for the exemplary description of the embodiments, it can be understood and effected by those skilled in the art that the invention is applicable to any device comprising a deflectable elongate body.

The invention claimed is:

1. A deflectable device comprising:
 a flexible elongate body;
 at least one electrically conductive U-shaped folded elongate member of a shape memory alloy material eccentrically positioned within the flexible elongate body to a longitudinal axis of the flexible elongate body;
 wherein a first portion comprising two free ends of the at least one folded elongate member is fixedly secured to a proximal portion of the flexible elongate body and a second portion comprising a fold of the at least one folded elongate member is fixedly secured to a distal portion of the flexible elongate body; and
 wherein the deflectable device is configured to change an orientation of the distal portion of the elongate body with respect to the proximal portion of the elongate body upon an electrical current flowing through the folded elongate member causing a change of a length of the folded elongate member.

2. The deflectable device of claim 1, wherein the first portion is a proximal end of the folded elongate member, and the second portion is a distal end of the of the folded elongate member.

3. The deflectable device of claim 2, further comprising: multiple folded elongate members.

4. The deflectable device of claim 3, further comprising: an electrical connection of the distal ends of the multiple folded elongate members.

5. The deflectable device of claim 1, wherein at least a leg of the folded elongate member is embedded in electrically insulating material.

6. The deflectable device of claim 5, wherein both legs of the folded elongate member are embedded in polytetrafluoroethylene.

7. The deflectable device of claim 1, wherein the folded elongate member is a flat wire or a strip.

8. A system for deflecting a deflectable device, comprising:
 a power control unit for providing electrical current;
 the deflectable device according to claim 1, wherein two legs of the at least one folded elongate member are adapted to be electrically connectable to the power control unit.

9. The system of claim 8, wherein:
 The deflectable device comprises multiple folded elongate members electrically connected at a distal portion;
 each leg of the multiple folded elongate members being adapted to be electrically connectable to the power control unit;
 the power control unit being configured to provide electrical current selectively to the legs of the multiple elongate members.

10. A method of deflecting a deflectable device, comprising:
 providing a deflectable device comprising:
  a flexible elongate body;
  at least one electrically conductive U-shaped folded elongate member of a shape memory alloy material eccentrically positioned within the flexible elongate body to a longitudinal axis of the flexible elongate body;
  wherein a first portion comprising two free ends of the at least one folded elongate member is fixedly secured to a proximal portion of the at least one flexible elongate body and a second portion comprising a fold of the at least one folded elongate member is fixedly secured to a distal portion of the flexible elongate body; and
  wherein the device is configured to change an orientation of the distal portion of the elongate body with respect to the proximal portion of the elongate body upon an electrical current flowing through the at least one folded elongate member causing a change of a length of the at least one folded elongate member;
 controlling the electrical current provided to the at least one folded elongate member within the deflectable device to change the orientation of the distal portion of the elongate body with respect to the proximal portion of the elongate body upon an electrical current flowing through the at least one folded elongate member causing a change of a length of the at least one folded elongate member.

11. A non-transitory computer-readable medium having stored a computer-executable program for deflecting a deflectable device, the computer program comprising program code means for causing a power control unit to selectively apply electrical power to the deflectable device to carry out the method of deflecting a device as claimed in claim 10, when the computer program is run on the power control unit for controlling the deflectable device.

\* \* \* \* \*